United States Patent [19]

Foley

[11] 4,182,912

[45] Jan. 8, 1980

[54] SYNTHESIS OF 5-BROMOPYROGALLOL 1,3-DIMETHYL ETHER

[75] Inventor: James W. Foley, Andover, Mass.

[73] Assignee: Polaroid Corporation, Cambridge, Mass.

[21] Appl. No.: 942,344

[22] Filed: Sep. 14, 1978

[51] Int. Cl.$^2$ ............................................. C07C 41/00
[52] U.S. Cl. .................................................... 568/649
[58] Field of Search ......................................... 568/649

[56] References Cited

PUBLICATIONS

Kohn et al., Jour. Org. Chem., vol. 12 (1947) 30-33.
Levine, Jour. Amer. Chem. Soc., vol. 48 (1926) 797-798.
Friedman et al., Jour. Org. Chem., vol. 23 (1958) 16-17.
Buu-Hoi, Chem. Abs., vol. 40 (1946) pp. 4669-4670.

*Primary Examiner*—Bernard Helfin
*Attorney, Agent, or Firm*—Sybil A. Campbell

[57] ABSTRACT

This invention is concerned with a method of preparing 5-bromopyrogallol 1,3-dimethyl ether by reacting equimolar amounts of pyrogallol 1,3-dimethyl ether and N-bromosuccinimide in a halogenated hydrocarbon solvent in the presence of monohydric alkyl alcohols, i.e., monohydric alkanols.

11 Claims, No Drawings

SYNTHESIS OF 5-BROMOPYROGALLOL 1,3-DIMETHYL ETHER

BACKGROUND OF THE INVENTION

1. Field of the Invention

This invention relates to a new method of preparing 5-bromopyrogallol 1,3-dimethyl ether.

2. Description of the Prior Art

M. Kohn and L. Steiner, *J. Org. Chem.*, 12, p. 30 (1947) have described the preparation of 5-bromopyrogallol 1,3-dimethyl ether by debromination of 4,5,6-tribromopyrogallol 1,3-dimethyl ether with zinc dust and acetic acid. Though numerous attempts have been made to synthesize the 5-bromo compound as the major or exclusive product directly from pyrogallol 1,3-dimethyl ether, they have been unsuccessful.

Because of the strong orienting influence of the methoxy groups, halogenation of pyrogallol 1,3-dimethyl ether occurs in the 4-position and only with an excess of halogenating agent sometimes occurs in the 5-position as well. Using 1 molar equivalent of bromine as the halogenating agent, A. A. Levine, *J. Amer. Chem. Soc.*, 48, p. 798 (1926) reported that the first bromine atom substitutes in the 4-position. D. Friedman and D. Ginsberg, *J. Org. Chem.*, 23, p. 16 (1958) reported that bromination of pyrogallol 1,3-dimethyl ether using 1 molar equivalent of N-bromosuccinimide (NBS) in carbon tetrachloride yields 4-bromopyrogallol 1,3-dimethyl ether. These authors also reported the formation of the 4,6-dibromo compound using 2 molar equivalents of NBS and the formation of the 4,5,6-tribromo compound using 3 molar equivalents of NBS. Upon repeating the experimental procedure of D. Friedman and D. Ginsberg using equimolar amounts of the pyrogallol and N-bromosuccinimide in boiling carbon tetrachloride, it was determined by nmr analysis of the crude reaction mixture that the 5-bromo compound also was formed but was present in only very minor amounts as compared to the amount of 4-bromo compound.

According to the present invention, it has been found that the 5-bromo compound can be obtained as the major product in the bromination of pyrogallol 1,3-dimethyl ether with NBS by conducting the reaction in the presence of certain alcohols. In a preferred embodiment, the bromination is conducted in the presence of sodium hydride in order to achieve a further increase in the formation of the desired 5-bromo product.

SUMMARY OF THE INVENTION

It is, therefore, the primary object of the present invention to provide a method of brominating pyrogallol 1,3-dimethyl ether with NBS to give 5-bromopyrogallol 1,3-dimethyl ether as the major reaction product.

Other objects of this invention will in part be obvious and will in part appear hereinafter.

The invention accordingly comprises the process involving the several steps and the relation and order of one or more of such steps with respect to each of the others and the scope of the application of which will be indicated in the claims.

For a fuller understanding of the nature and objects of the invention, reference should be had to the following detailed description.

DETAILED DESCRIPTION OF THE INVENTION

Specifically, the method of the present invention comprises reacting equimolar amounts of pyrogallol 1,3-dimethyl ether and N-bromosuccinimide in a halogenated hydrocarbon solvent containing a monohydric alkanol in an amount sufficient to give 5-bromopyrogallol 1,3-dimethyl ether as the major reaction product.

The alkanol employed may be a branched or straight-chain monohydric alkanol and usually is a monohydric alkyl alcohol containing 1 to 6 carbon atoms, for example, methanol, ethanol, propanol, iso-propanol, n-hexanol, s-butanol and t-butanol. To achieve formation of the desired 5-bromo compound in a major proportion as compared to the 4-bromo compound, the alkanol is added to the halogenated hydrocarbon solvent in an amount between about 0.5% and 10.0% by volume, and usually is employed in an amount between about 0.5 and 1.0% by volume.

Illustrative of the halogenated hydrocarbons that may be employed as the reaction solvent are carbon tetrachloride, methylene chloride, bromoform and chloroform. The amount of solvent is not critical, but should be sufficient to dissolve the reactants which amount may be readily determined empirically. Preferably, the reaction solvent is a chlorinated hydrocarbon.

Though the reaction temperature may vary over a relatively wide range including reflux, it is preferred to conduct the bromination reaction at lower temperatures between about −70° and 20° C. and preferably below 0° C., since the 5-bromo compound is obtained in better yields in the lower temperature range.

To achieve further increases in the yield of the desired 5-bromo product, the subject bromination preferably is conducted in the presence of sodium hydride in addition to the monohydric alkanol. In this preferred embodiment, the sodium hydride is conveniently used as a 50% oil dispersion in an amount of about 0.01 to 0.05 mole NaH per mole of pyrogallol.

The following examples are given to further illustrate the present invention and are not intended to limit the scope thereof.

EXAMPLE 1

Preparaton of 5-bromopyrogallol 1,3-dimethyl ether having the formula

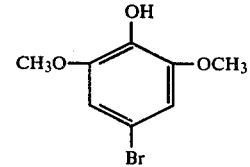

To a 3 liter flask equipped with a mechanical stirrer, thermometer and nitrogen inlet was added 154 g. (1 mole) of pyrogallol 1,3-dimethyl ether and 1.5 liters of CHCl$_3$. To this solution was added 0.5 g (0.01 mole) of NaH (50% oil dispersion). The solution was stirred while cooling to −45° C. with a dry-ice acetone bath and 178 g. (1 mole) of powdered N-bromosuccinimide was added rapidly. There was a slight exotherm. The reaction mixture was then stirred for 1 hour at −35° C., heated to room temperature over the next 30 minute period, and finally refluxed for 30 minutes. The CHCl$_3$ was removed under reduced pressure and the residue solidified. The tan solid was broken up and stirred well with 2 liters of ether. This was filtered and the residue[1] washed well with ether. The ether was evaporated under reduced pressure to yield a tan solid. The solid was placed in a 10 liter flask with 6 liters of ligroin (boiling range 90°–110° C.) and heated with stirring to 80° C.[2]. The hot solution was decanted from the brown oil and was filtered through a pre-heated[3] celite pad, using an aspirator, into a pre-heated flask. The light yellow solution was allowed to cool at room temperature for 3 hours[4]. The white wooly needles were filtered off and dried to yield 110 g. The mother liquor was evaporated to one-half its original volume, reheated to dissolve any solid which precipitated and the hot solution worked up as in the above step. A second crop of 30 g. was collected to give the title compound in a total yield of 140 g. (61%) melting range 99.5°–100° C.

[1] The succinimide is insoluble in ether.
[2] Most of the brown oil remaining was an impurity.
[3] This was accomplished by simply pouring hot ligroin through the celite pad under reduced pressure.
[4] If a brown oil precipitates initially, then the ligroin solution is filtered through the celite again before cooling further. Standing for more than 3 hours may cause the impurity to co-precipitate.

EXAMPLES 2–13

In Examples 2 to 13 and the controls listed in the following Table, the pyrogallol 1,3-dimethyl ether and N-bromosuccinimide were reacted in equimolar proportions at the temperature designated using the designated % by volume of the specified alkanol in the specified solvent. Where appropriate, the amount of sodium hydride (NaH) employed also is specified.

By "proportion yield" is meant the proportion of 5-bromopyrogallol 1,3-dimethyl ether compared to 4-bromopyrogallol 1,3-dimethyl ether in % as measured in the crude reaction mixture by nmr analysis.

By "crude yield" is meant the overall yield of 5-bromopyrogallol 1,3-dimethyl ether in % as measured in the crude reaction mixture by nmr analysis.

TABLE

| Example No. | Proportion Yield | Crude Yield | Reaction Solvent | Temp. °C. | *Alkanol % by vol | NaH mole |
|---|---|---|---|---|---|---|
| 2 | 65.9 | 48 | CHCl$_3$ | +20° | EtOH 0.75% | 0.01 |
| 3 | 88.1 | 75 | " | −70° | " | " |
| 4 | 87.5 | 72 | " | −20° | " | " |
| 5 | 82.6 | 73 | " | −20° | " | — |
| 6 | 80.0 | 73 | " | −20° | " | — |
| Control | 16.8 | 14 | " | −20° | — | — |
| 7 | 62.1 | 54 | CH$_2$Cl$_2$ | −20° | EtOH 1.0% | — |
| 8 | 67.6 | 52 | " | −20° | EtOH 2.0% | — |
| Control | 39.3 | 38 | " | −20° | — | — |
| 9 | 68.3 | 61 | CCl$_4$ | −20° | EtOH 1.0% | — |
| 10 | 65.7 | 53 | " | −20° | EtOH 10.0% | — |
| 11 | 73.0 | 63 | " | −20° | n-BuOH 1.0% | — |
| 12 | 61.8 | 58 | " | −20° | iso-BuOH 1.0% | — |
| 13 | 67.5 | 53 | " | −20° | t-BuOH 1.0% | — |
| Control | 22.3 | 21 | " | −20° | — | — |

*In the alkanols listed, EtOH = ethanol; n-BuOH = n-butanol; iso-BuOH = isobutyl alcohol; and t-BuOH = tert-butanol.

Though it has been found that aromatic and substituted alkyl alcohols also are useful in enhancing the formation of the desired 5-bromo product, the proportion of 5-bromo to 4-bromo compound was not sufficient to permit facile isolation from the crude reaction mixture by simple crystallization techniques. For example, when equimolar amounts of the pyrogallol and NBS were reacted at −20° C. in carbon tetrachloride containing 1.0% by volume of benzyl alcohol, the proportion yield was 43.5 (% by nmr). Under the same conditions but using 1.0% by volume of 2-methoxyethanol, the proportion yield was 41.2 (% by nmr).

As mentioned above, the experimental procedure of D. Friedman and D. Ginsburg was repeated. Equimolar amounts of the pyrogallol and N-bromosuccinimide were reacted in carbon tetrachloride at reflux. The proportion yield obtained was 15.5 (% by nmr) for the 5-bromo compound and a crude yield of about 15.0 (% by nmr).

The brominated compound produced by the subject method is useful, e.g., as a starting material for the photographic optical filter agent precursors forming the subject matter of copending U.S. patent application Ser. No. 836,006 of Stanley M. Bloom et al filed Sept. 23, 1977, now U.S. Pat. No. 4,139,381 issued Feb. 13, 1979. As discussed therein, the subject compound after blocking the —OH with methoxymethyl is converted to the corresponding Li compound, and 2 moles of the Li compound is reacted with saccharin pseudo-chloride to give the 3,3-disubstituted sulfamphthalein followed by N-acylation with ClCOO(CH$_2$)$_2$CN and deblocking of the —OH to yield the said precursor.

Since certain changes may be made in the hereindescribed subject matter without departing from the scope of the invention herein involved, it is intended that all matter contained in the above description and examples be interpreted as illustrative and not in a limiting sense.

What is claimed is:

1. A method of preparing 5-bromopyrogallol 1,3-dimethyl ether which comprises reacting equimolar amounts of pyrogallol 1,3-dimethyl ether and N-bromosuccinimide at a temperature between about −70° and 20° C. in a halogenated hydrocarbon solvent containing a monohydric alkanol in an amount sufficient to give said 5-bromopyrogallol 1,3-dimethyl ether as the major reaction product.

2. A method as defined in claim 1 wherein said alkanol is present in said solvent in an amount between about 0.5% and 10.0% by volume.

3. A method as defined in claim 1 wherein said solvent is chloroform.

4. A method as defined in claim 1 wherein said solvent is methylene chloride.

5. A method as defined in claim 1 wherein said solvent is carbon tetrachloride.

6. A method as defined in claim 1 wherein said alkanol is ethanol.

7. A method as defined in claim 1 wherein said alkanol is n-butanol.

8. A method as defined in claim 1 wherein said alkanol is isobutyl alcohol.

9. A method as defined in claim 1 wherein said alkanol is tert-butanol.

10. A method as defined in claim 1 wherein said reaction is conducted in the presence of sodium hydride.

11. A method as defined in claim 10 wherein said sodium hydride is present in amount between about 0.01 and 0.05 mole per mole of pyrogallol 1,3-dimethyl ether.

* * * * *